United States Patent [19]

Heimreid

[11] Patent Number: 5,099,992
[45] Date of Patent: Mar. 31, 1992

[54] ARRANGEMENT IN CONNECTION WITH A RACK FOR ORDERLY STORAGE AND/OR FOR KEEPING SYRINGES WITH A LUER TIP READY FOR USE

[76] Inventor: Bent Heimreid, N-3942 Skjelsvik, Junoveien 19, Norway

[21] Appl. No.: 552,122

[22] Filed: Jul. 13, 1990

[30] Foreign Application Priority Data

Nov. 3, 1989 [NO] Norway .................. 894377

[51] Int. Cl.$^5$ .................................... B65D 83/10
[52] U.S. Cl. .................. 206/366; 206/370; 206/438; 604/192
[58] Field of Search ............ 209/363, 364, 365, 366, 209/370, 438, 562, 563, 564; 604/192; 211/71, 74

[56] References Cited

U.S. PATENT DOCUMENTS

| | | | |
|---|---|---|---|
| 964,406 | 7/1910 | Dewitt | 206/366 |
| 2,666,967 | 1/1954 | Poitras | 206/366 |
| 2,790,547 | 4/1957 | Sutton | 206/562 |
| 3,439,796 | 4/1969 | Zykoski | 206/366 |
| 3,444,860 | 5/1969 | Harrell | 206/364 |
| 3,649,464 | 3/1972 | Freeman | 206/562 |
| 4,420,085 | 12/1983 | Wilson et al. | 206/370 |
| 4,596,562 | 6/1986 | Vernon | 206/366 |
| 4,658,957 | 4/1987 | Guth et al. | 206/563 |
| 4,717,386 | 1/1988 | Simmons | 604/192 |
| 4,832,842 | 5/1989 | Limb | 206/562 |
| 4,844,249 | 7/1989 | Coulombe | 206/563 |
| 4,850,484 | 7/1989 | Denman | 206/563 |
| 4,875,583 | 10/1989 | Nosanchuk | 206/563 |
| 4,890,734 | 1/1990 | Gach | 206/366 |
| 4,973,315 | 11/1990 | Sincock | 206/365 |

FOREIGN PATENT DOCUMENTS

434473 1/1925 Fed. Rep. of Germany ...... 206/562

Primary Examiner—David T. Fidei
Attorney, Agent, or Firm—Cushman, Darby & Cushman

[57] ABSTRACT

A block-shaped rack has a plurality of pairs of opposite faces. At least two opposite faces are provided with outwardly projecting, peg-like luer cone tip replicas. A plurality of bushings is provided, each having two axially oppositely opening luer cone receptacle replicas. In use, luer cone-tipped syringes can be removably mounted on the rack using the bushings as adapters. The bushings may be supplied packaged in a sterile condition. If the receptacles on a bushing are intercommunicated within the bushing, the bushing may act as an adapter for two syringes, so that fluid can be transferred from one to the other.

9 Claims, 5 Drawing Sheets

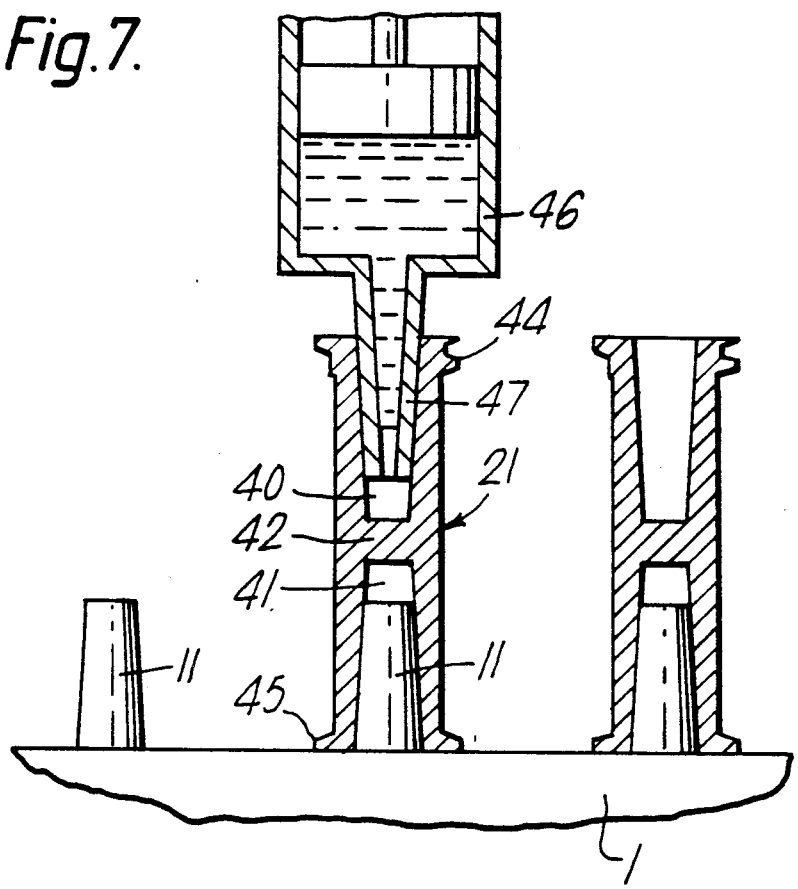
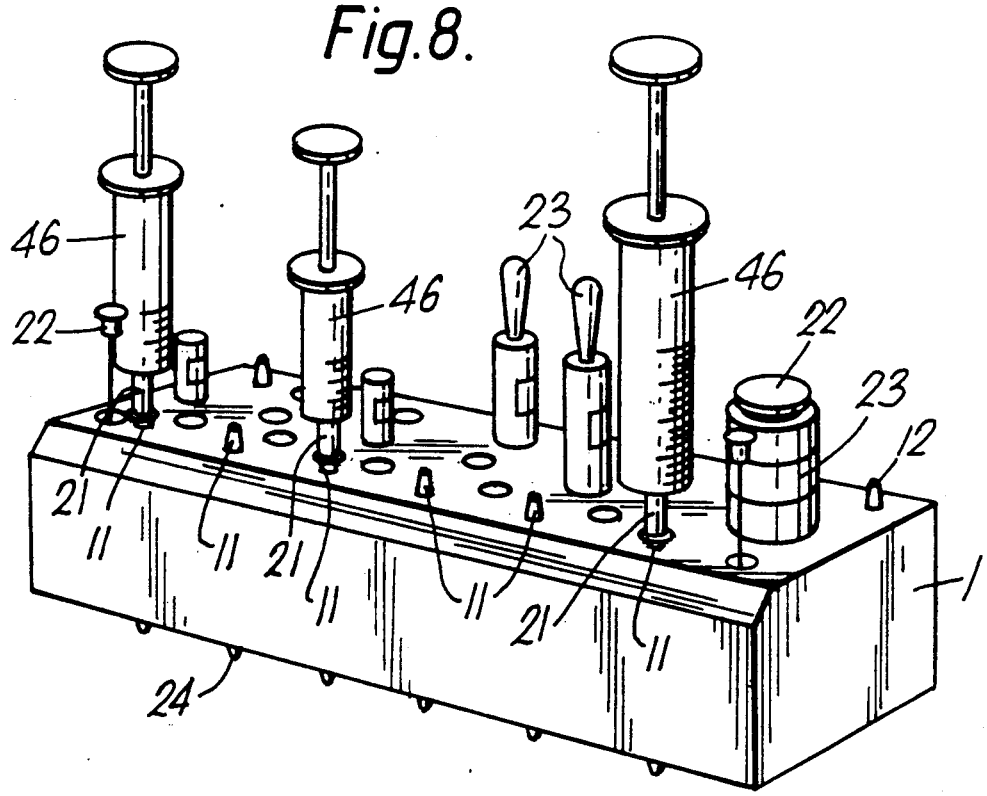

Fig.11.
Fig.12.
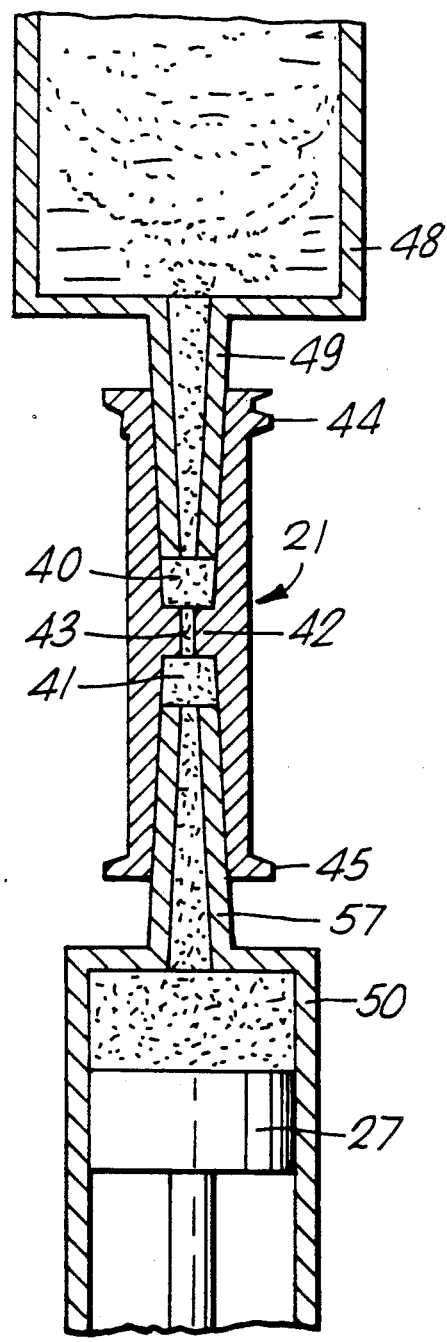
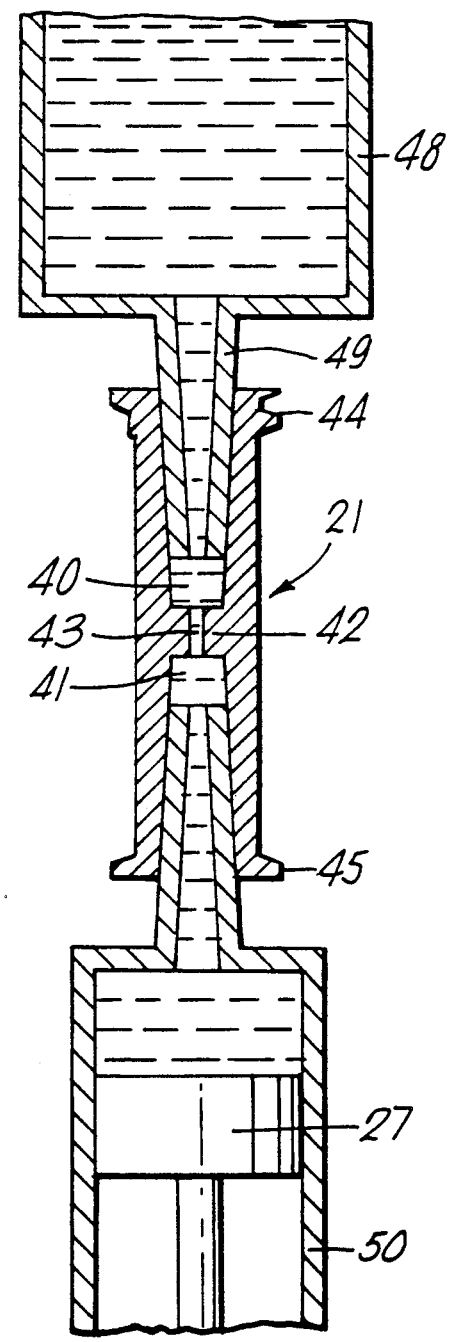

ARRANGEMENT IN CONNECTION WITH A RACK FOR ORDERLY STORAGE AND/OR FOR KEEPING SYRINGES WITH A LUER TIP READY FOR USE

BACKGROUND OF THE INVENTION

The invention relates to an arrangement in connection with a rack for orderly storage and/or for keeping of syringes, each with a luer projection ready for use, the rack also comprising receptacle means for the syringes.

Syringes are used in all departments of the health sector. Some people inject themselves, e.g. diabetes patients, but in most cases the injection, i.e. the contents of the syringe, are administered by a medical practitioner or a nurse.

The patient/user receives the injection either subcutaneously (under the skin), intramuscularly (in the muscle), or intravenously (via the vein system). The syringe contents (medicament) may be administered by connecting the syringe with an intravenous cannula or by providing the syringe with a syringe needle which is introduced under the skin or into a muscle. Injections may also be administered in spinal/epidural ducts.

In any case, every object to be used must be sterile.

Syringes are filled by sucking the contents of an ampule or another container through a suction cannula. Such medicament suction may, e.g., be carried out in the patient's home, in separate syringe medicament rooms, in surgical theatres, wards for intensive care, etc.

In a surgical theatre, syringes filled with a medicament are e.g. placed on an anaesthetics table. During administration to the patient and maintenance of anesthelization, the medicament is administered as required. Use of several different syringes during one anesthetization is not uncommon, and this means that there will be a plurality of syringes, ampulses and needles, etc., in circulation. Conditions may easily become slightly chaotic, since may different medicaments are also used. The hazard of making an error or administering a wrong medicament will increase when syringes, after some time, lie about in a mess, e.g. in an acute situation. This may happen in spite of the fact that each syringe should be marked with the kind of medicament to be administered.

As known, use of syringes generally requires the strictest possible hygiene, and the syringe or syringes, thus, must be kept under maximum hygienic conditions and safety against confusion, from the moment they are filled and until they are used. A common procedure today is that a sterile stop or plug is provided on the syringe tip upon the syringe being filled, and if the syringe tip is sterile. The syringe needle is kept in a sterile wrapping until it is to be used. Another procedure is to keep the syringe needle on the syringe, e.g. inserted in the ampule with the medicament to be used.

In the course of daily routines filled and ready syringes are kept on a tray or the like in a refrigerator, or on the patient's bedside table, etc. before the injection is administered to the patient. Often, it happens that the syringe is not reposing where it was put, but rolls about on the tray or may even fall onto the floor. Needles and/or tips then often become less than sterile. The syringes have no firm bed and conditions easily get chaotic. The hygienic situation, as mentioned, may also become hazardous.

For inocculation or for administration of injections to many persons, a plurality of equal syringes are often prepared. They are put side-by-side. It is unsatisfactory to have syringes lying about freely, because they may roll about and/or be touched in an undesirable manner, so that sterility is lost. It is even more difficult to maintain necessary hygienic conditions when there are different medicaments to be administered at the same time.

The conventional system as regards storage of syringes with medicaments, from the moment the syringe is filled with the medicament and until the latter is administered, is thus not satisfactory. There is a hazard of sterility being lost, since routines do not comprise a firm and/or steady holder for the syringes. There is a hazard of administrating a wrong medicament and/or a wrong dosis. In acute situations it will often be difficult to take in everything at a glance, e.g. when several filled syringes are placed together in a bowl or the like in a refrigerator. Some medicaments are stored for up to 24 hours after having been sucked in a sterile manner into a syringe, with a sterile plug/needle on the tip. This, obviously, does not improve conditions are regards hygiene. One of the known systems used to day, luer plugs, are bushing members having a cone shaped portion at one end with a finishing external locking thread. At the other end there is a bushing portion shaped with a slightly larger diameter and an internal locking thread, adapted to the cone shaped locking thread. The cone has a conical blind bore, adapted to the conical shape of the syringe tip, and the bushing member has an internal coaxial conical plug which is adapted, to the conical blind bore in the locking cone.

When a medicament is to be sucked into a syringe from an ampule or the like, this is commonly carried out through a suction cannula which is placed onto the syringe tip. When the syringe has been filled, the suction cannula is removed and a sterile luer plug is provided instead. When the medicament is to be administered, the luer plug is removed and the syringe tip is provided with a needle or a cannula.

SUMMARY OF THE INVENTION

It is a main object of the present invention to provide an arrangement, in connection with a rack for orderly storage and/or for keeping syringes ready for use, with the aim of achieving controlled and sterile conditions. Another object of the invention is to provide an arrangement in connection with a rack for orderly storage and/or for keeping syringes, needle, ampules and the like prepared for use.

The invention is based on known technology, racks being known for receiving syringes, needles, ampullae, and the like.

According to the invention an arrangement in connection with a rack is, thus, provided for orderly storage and/or for keeping syringes with a luer tip or a luer locking tip ready for use, which rack comprises receptacle means for the syringes. The syringe receptacle means comprise spigots which are integrated in the rack, and bushing members which may be placed on respective spigots. The bushing members are shaped for receiving the luer tips of the syringes.

The bushing member may have an inner transversal wall, so that both tip receptacle means are physically separated, or the transveral wall may be omitted, or it may, if desired, have a through hole. It is this open bushing member design which is of special interest, since it may be part of an advantageous transferring system for transferring a dosage of a medicament from one syringe to another mixture of two components/medicaments or for eliminating air.

Each bushing member may advantageously at its ends be provided for being locked to a luer thread in a bushing portion of a luer plug.

In a suitable embodiment of the invention, the spigots are provided in one or a plurality of rows on a block, shaped rack. Such a rack will be steady and compact. An arrangement of the spigots on two (or more) opposite lateral block faces is rendered possible. The rack will, thus, be utilized in the best possible manner and it may be made more universally applicable if spigots are arranged on one lateral block face, whereas spigots and other receptacle means—for needles, ampules and the like—are placed on the opposite lateral block face.

The last-mentioned embodiment is a preferred embodiment because it provides for orderly storage and/or for keeping ready syringes with associated needles, ampules, and the like.

The filled syringes may, e.g., be placed in one row, whereas associated ampules are placed in a parallel receptacle row. Required syringe needles may also be placed in a parallel row. In this manner good order and survey is achieved.

BRIEF DESCRIPTION OF THE DRAWINGS

The invention is disclosed in more detail below with reference to the accompanying drawings, in which:

FIG. 7 shows a portion of the rack of FIGS. 1 and 2, with a provided bushing member (in section), and with a syringe shown inserted in place in the bushing member, FIG. 8 is a perspective view of the rack, FIG. 11 shows two syringes which are connected with the bushing member according to FIGS. 5 and 6, for mixture of two medicaments, and FIG. 12 shows two syringes which are connected with the bushing member according to FIGS. 5 and 6, for transfer of medicament from one syringe to the other.

DETAILED DESCRIPTION

The rack shown in FIGS. 1, 2, 7 and 8 is block-shaped. Block 1 suitably consists of a sterilizable material, e.g. a suitable plastic material.

Block 1 has four lateral block faces, 2, 3, 4, and 5, and two block end faces, 6 and 7.

Figure 1:
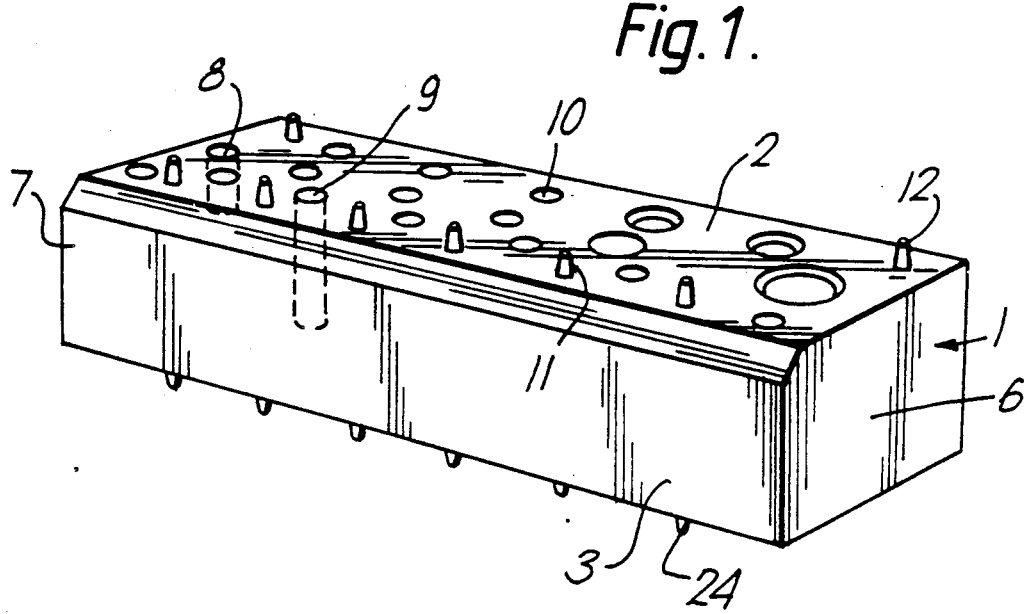
FIG. 1 is a perspective view of a rack embodying principles of the present invention.

In one lateral block face 2, as shown in FIG. 1, several recesses, 8, 9, and 10 are formed. On the same block face 2 there are also several projecting spigots 11, 12. (The term "spigot" is used herein to denote an axially elongated, peg-like boss, which is preferably externally tapered, e.g., frustoconically tapered, so as to diminish in external diameter from the block face on which it is based, towards a free outer end.)

Spigots 11 are arranged in a row along the edge, in the present instance, there are six spigots 11. On the opposite face edge, two spigots 12 are placed, one at each block end. In parallel with and inside the row of spigots 11, a row of relatively deep recesses or depressions 9 is provided.

In parallel with the row of depressions 9, a row of slightly more shallow depressions or recesses 8 is provided. Behind the row of depressions 8 there is a row of shallow/deep depressions or recesses 10.

The deep recesses 9, which may, e.g., be blind bores, all have the same diameter in the preferred embodiment and are intended for receiving syringe needles.

The next row comprises depressions or blind bores 8 of varying diameters, in this case increasing towards the right side in FIG. 1, which bores are intended for receiving ampules.

Depressions 10, which may be shallow or deep, are intended for receiving other equipment that might be required, e.g. extra ampules, medicament containers, needles, etc.

Spigots 11 and 12 are intended for receiving syringes, and the special function of the spigots will be explained in detail below.

First, the structure and function of a luer plug will be described in more detail. Such a typical and known luer plug is shown in FIGS. 3 and 4.

Figure 3:
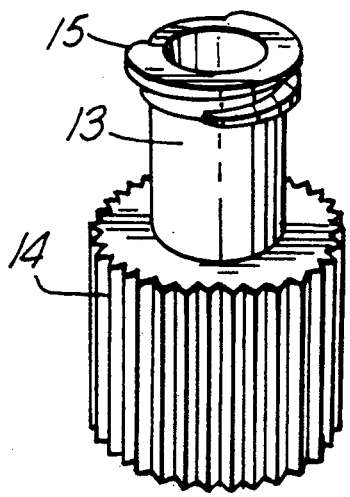
FIG. 3 is a perspective view of a luer plug.
Figure 4:
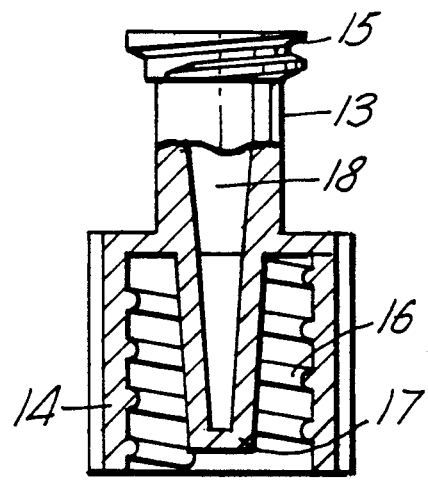
FIG. 4 shows a partial section through the plug of FIG. 3.

The luer plug shown in FIGS. 3 and 4 has a locking spigot portion 13 and a bushing portion 14. At the end of the locking spigot a locking thread 15 is provided. The latter is intended for threaded and locking cooperation with an internal thread 16 in a bushing portion 14. Centrally in bushing portion 14, there is a spigot 17 which is slightly conical externally. In locking spigots 13 a corresponding slightly conical bore 18 is provided. The slightly conical bore 18 and the slightly conical spigot 17 are mutually adapted, so that the spigot 17 on a luer plug may be inserted into conical bore 18 in a sealing manner. Slightly conical bore 18 is adapted to a so called luer cone, which is e.g. found on a syringe tip. This means that a syringe tip may be inserted into conical bore 18 for sealing cooperation with the luer plug. Locking thread 15 and internal thread 16 are mutually adapted so that locking spigot 13, 15 on a luer plug may be screwed into and cooperate with thread 16, with internal spigot 17 passing into conical bore 18 of an adjacent plug.

In the other recesses or bores, and on spigot 11, possibly also on spigot 12, other components may be arranged, e.g. additional ampules, syringes, needles, etc.

Figure 2:
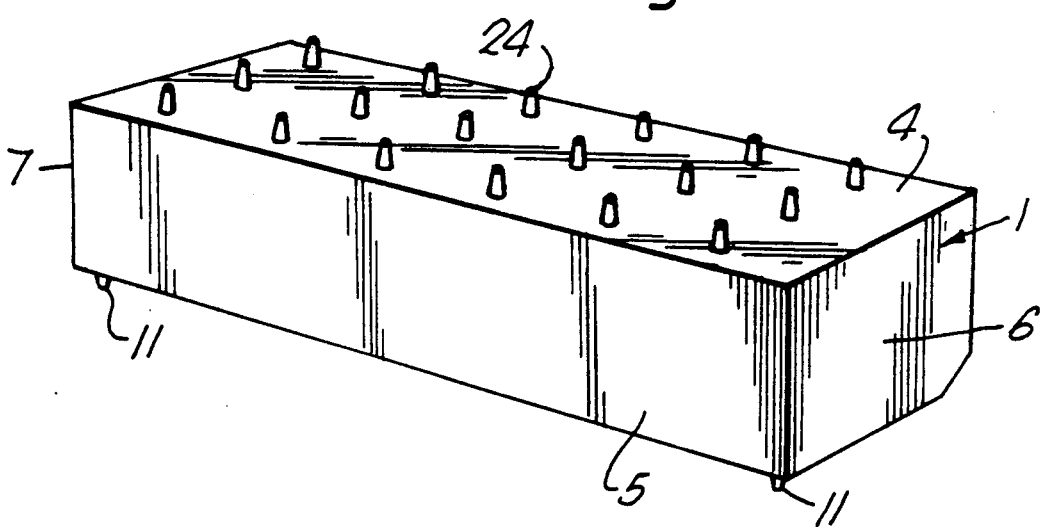
FIG. 2 shows the rack of FIG. 1 as seen from below.

On what may be called the lower side of rack 1 in FIG. 1, a total of eighteen spigots 24 is shown. They correspond to spigots 11 and 12 as to shape and function and are provided for the same reason. Rack side 4, shown in FIG. 2, is especially suitable when a large number of preferably similar syringes is to be prepared for use, e.g. in connection with inocculation. In this case eighteen syringes may be provided in rows in the rack. Associated needles may, if desired, be placed in receptacle bores in block face 4, or they may be placed in a bowl wrapped in a sterile manner until they are to be used.

When the rack is used as shown in FIGS. 1 and 8, the rack or block 1 rests on spigots 24, and conversely, when the rack is used as shown in FIG. 2, it rests in a stable and steady manner on spigots 11, 12.

Spigots 11 and 12 are intend for receiving special bushing members 21, see FIGS. 7 and 8.

Figure 6:
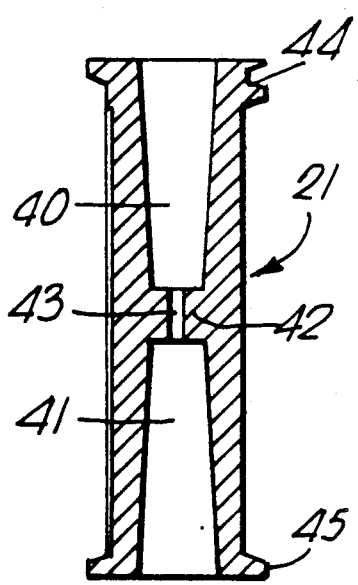
FIG. 6 is a longitudinal section of the bushing member of FIG. 5.
Figure 5:
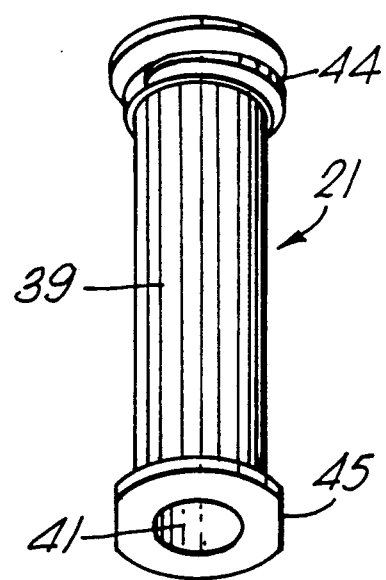
FIG. 5 shows a bushing member in a perspective view, for use on the rack of FIGS. 10 and 11.

One such a bushing member 21 is shown in more detail in FIGS. 5 and 6.

It will appear from FIGS. 5 and 6 that this special bushing member is an externally ridged 39 circular cylinder, which at each end is provided with a plug receptacle means 40, 41, intended for receiving a form-fitting luer tip or luer cone. Receptacle means 40, 41 are separated by a transversal wall or partition 42. In the embodiment shown in a sectional view in FIG. 6, the partition 42 has a throughbore or a through hole 43, but the partition may also be unperforated so that the receptacle means are physically separated. See FIGS. 7 and 8.

Through opening 43 is of special interest in connection with utilization of the bushing member in a transfer system for transferring medicaments from one syringe to another. This is disclosed in more detail below. Bushing member 21 has a flange-shaped locking thread 44, 45 at each end intended for cooperation with a luer thread in a bushing-shaped portion fo a luer plug see, e.g., FIG. 10. In this connection one should also refer to what is mentioned above in regard to luer plugs and the special design of such plugs.

In FIG. 7, a portion of a rack 1 with spigots 11 is shown. On two spigots, a bushing member 21 is provided. One one bushing member 21, shown in longitudinal section, an inserted syringe 46 is indicated. Syringe 46 has a luer tip or cone 47 fitting into receptacle means 40 in the bushing member. Correspondingly, spigot 11 is adapted to be receptacle means 41. The spigot, as mentioned before, is advantageously shaped like a luer cone, i.e. corresponding to cone 47.

When a syringe 46 is to be placed in rack 1, a sterile-wrapped bushing member 21 is removed from its wrapping and placed on spigot 11, whereon syringe tip 47 may be inserted into slightly conical receptacle means 40, as shown in FIG. 7. In this manner, the syringe will be kept in the rack in a sterile manner.

FIG. 8 shows an example of how rack 1 may be used. On three spigots 11, a respective bushing member 21 is placed and a syringe 46 is placed in each of members 21. In the recesses or bores, associated syringe needles 22 and ampules 23, etc., are placed.

On what may be called the rack underside in FIG. 1, a total of eighteen spigots 24 is shown. They correspond to spigots 11 and 12 as to shape and function, and are provided for the same reason. Rack side 4 shown in FIG. 2 is especially suitable when a larger number of preferably identical syringes is to be prepared for use, e.g. in connection with inocculation. In this case, eighteen syringes may be placed in rows on the rack. Associated needles may, if desired, be placed in receptacle bores (not shown) in block face 4, or they may be placed in a bowl in their sterile wrappings, ready for use. When the rack is used as shown in FIGS. 1 and 8, the rack or block rests on spigots 24, and conversely, when the rack is used as shown in FIG. 2, it will rest in a stable and steady manner on spigots 11, 12.

As mentioned, bushing member 21 in the embodiment shown in the sectional view of FIG. 6, in which the internal partition has a through bore, may additionally be utilized as a component in an advantageous manner when it is desirable to transfer a medicament from one syringe to another. Such a connection of two syringes is shown in FIGS. 9-12.

Figure 9:
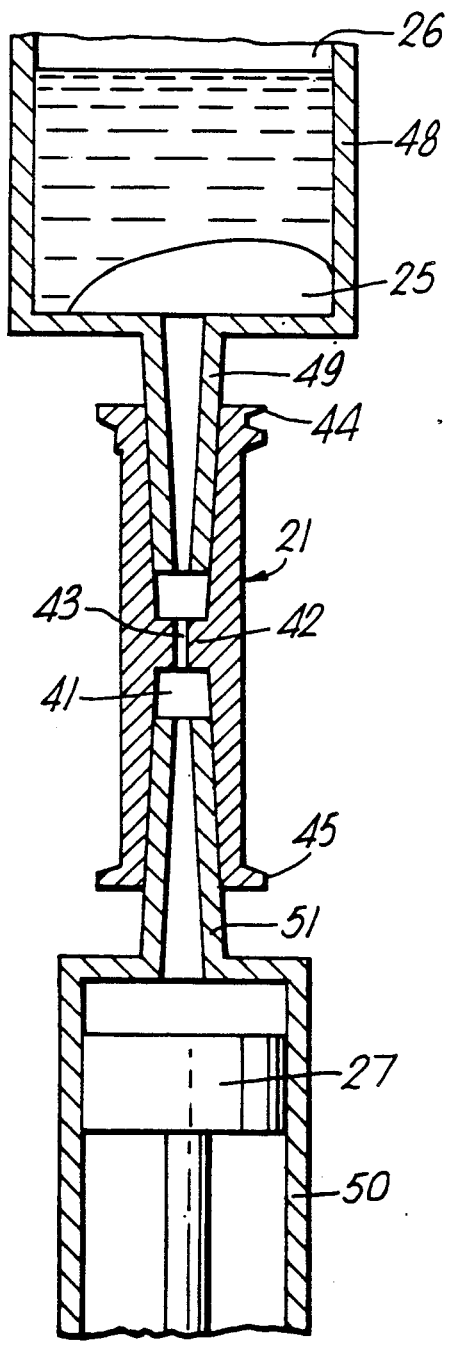
FIG. 9 shows two syringes which are connected with the new bushing member according to FIGS. 5 and 6.

In the sectional views of FIGS. 9, 11 and 12, a syringe 48 with a syringe tip 49 and a syringe 50 with a syringe tip 51 are shown. The two syrings are connected by the aid of bushing member 21, with one syringe tip 49, as shown, being inserted into receptacle means 40, and the other syringe tip 51 being inserted in conical receptacle means 41.

At present no practical and inexpensive coupler means for two syringes is known. The invention provides a remedy. To mix liquid/liquid or medicaments from one syringe in another, a syringe needle is used at present to be inserted in the orifice of the other syringe. The receiving syringe must then be prepared in advance to receive the injection/liquid volume.

It is also known, e.g., to use a three-wat cock, but such a concept is not very practical and it is expensive, at the same time as there is a hazard of making wrong connections. There is, thus, a strong demand for a simple, closed system (coupler) for the syringes, and this is the problem which is solved by the structure shown in FIGS. 9-12.

According to another known concept for mixing two components, two syringes are placed in parallel, side-by-side. The contents are mixed when a common connection between both syringe plungers is depressed. This arrangement is not very satisfactory, both from environmental and health considerations. There is no closable connection between the units, which connection would be most desirable to have.

An application of interest would be when it is desirable to dose small volumes of medicament from a large filled syringe into a smaller one for accurate dosage. There is no satisfactory system for such applications today.

In order to eliminate air collecting in the syringe, there is conventionally no good remedy. The technique heretofore has been to squirt a little medicament out of the syringe from which it is desired to remove air. This results in contamination of the environment, which may be a very serious matter, since it is often a question of substances that are very harmful to other persons than the patient. The system with coupler means as shown in FIGS. 2-12 may be helpful in this case too.

When syringes 48, 50 are connected as shown in FIGS. 9, 11 and 12, the contents of the syringes may be moved from one syringe to the other and back (FIG. 11) by the aid of plungers 26, 27, and, in addition to a desired transfer, to achieve a more accurate dosage (FIG. 12), the medicaments may also be mixed and air 25 may, obviously, be removed from one syringe by being transferred to the other syringe (FIG. 9).

Figure 10:
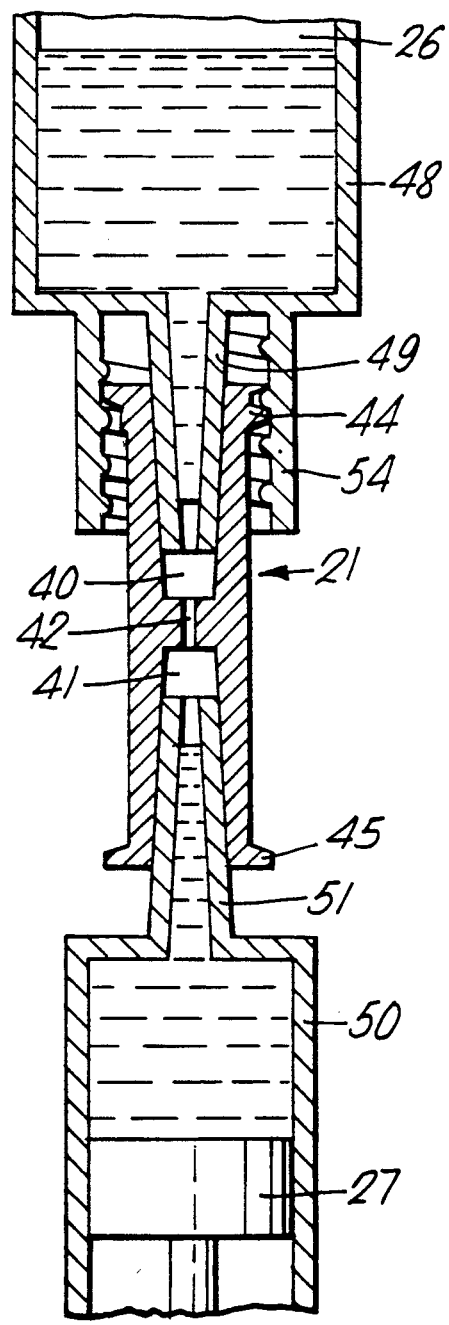
FIG. 10 shows two syringes which are connected with a bushing member having a closed transversal wall, and with one syringe being provided with a luer connection.

A bushing member with a solid partition 42 may advantageously be used for a closure member for one or two syringes. It will be especially advantageous to use the bushing member for a closure means when the bushing member has a luer locking thread at one or both ends, see FIGS. 5 and 6, whereas the syringe has a bushing-shaped portion about its luer cone, corresponding to the, locking bushing portion known from a luer plug. Such a possible embodiment of the syringe is shown in FIG. 10, showing a modified syringe 48 with a luer tip 49 surrounded by an internally threaded bushing portion 54, which corresponds to the bushing portion known from luer plugs. See the above description of a luer plug. Bushing member 21 can then be screwed in place inside bushing-shaped portion 54, with luer thread 44 being screwed into bushing 54. In this manner, the bushing member may be tightened well against cone 49 and is kept in place in its locking/closing position. The bushing member with a tight partition 42 may also, advantageously, be used for all couplings which are surrounded by an internally threaded bushing-shaped portion 54.

A possible elaboration which is not practically possible to illustrate in the drawings is the possibility of using colour codes for the various components.

Having described my invention, I claim:

1. Apparatus for supporting luer cone-tipped syringes in an orderly manner, comprising:
   a rack having at least one face;
   a plurality of luer cone tip-shaped pegs each provided on said rack so as to project taperingly outwardly from a respective said face; and
   a plurality of axially elongated bushing members, each having two axially oppositely opening luer cone receptacle-shaped recesses provided so as to project flaringly outwardly in axially opposite directions and open through axially opposite ends of the respective said bushing member;
   each said recess being sized and shaped to be alternatively removably telescopically recieved on a respective said luer cone tip-shaped peg on said rack and to removably telescopically receive a luer cone tip of a luer cone-tipped syringe.

2. The apparatus of claim 1, wherein:
   at least some of said luer cone tip-shaped pegs are arranged in a row on said face of said rack.

3. The apparatus of claim 1, wherein:
   said rack has at lesat two laterally opposite faces including said one face and a respective opposite face; and
   others of said luer cone tip-shaped pegs are provided on said respective opposite face.

4. The apparatus of claim 3, further including:
   means defining a plurality of receptacles in at least one said face of said rack, said receptacles being arranged for removable receipt of objects.

5. The apparatus of claim 1, wherein:
   on at least one of said bushing members, said luer cone receptacle-shaped recesses are physically isolated from one another internally of the respective said bushing member by transverse wall means of the respective said bushing member.

6. The apparatus of claim 1, wherein:
   on at least one of said bushing members, said luer cone receptacle-shaped recesses are physically interconnected through an orifice formed in a transverse wall means of the respective said bushing member.

7. The apparatus of claim 1, wherein:
   at least one of said bushing members is externally provided with a band of helical luer threading at each of said opposite ends thereof.

8. The apparatus of claim 1, wherein:
   at least one of said bushing members is sealingly enclosed in a sterile state within removable packaging material.

9. The apparatus of 1, further comprising:
   at least two of said bushing members having one said luer receptacle-shaped recess thereof telescopically received on a respective said one of said luer cone tip-shaped peg on said rack; and
   two luer cone-tipped syringes, each having a luer cone tip thereof telescopically received in a respective other of said luer receptacle-shaped recesses of said two bushing members.

* * * * *